United States Patent [19]

Harting et al.

[11] Patent Number: 4,522,829
[45] Date of Patent: Jun. 11, 1985

[54] 1-(P-2-ISOPROPOXYETHOXYMETHYL-PHENOXY)-3-ISOPROPYLAMINO-PROPAN-2-OL FOR DECREASING THE INTRA-OCULAR PRESSURE AND AN OPHTHALMIC PREPARATION THEREOF

[75] Inventors: Jürgen Harting; Andreas Fuchs, both of Darmstadt, Fed. Rep. of Germany

[73] Assignee: Merck Patent Gesellschaft mit Beschränkter Haftung, Darmstadt, Fed. Rep. of Germany

[21] Appl. No.: 393,914

[22] Filed: Jun. 30, 1982

[30] Foreign Application Priority Data

Jun. 30, 1981 [DE] Fed. Rep. of Germany ....... 3125636

[51] Int. Cl.$^3$ ............................................ A61K 31/135
[52] U.S. Cl. .................................... 514/652; 514/913
[58] Field of Search ........................ 424/330; 564/349

[56] References Cited

U.S. PATENT DOCUMENTS

| | | | |
|---|---|---|---|
| 3,996,382 | 12/1976 | Berntsson et al. | 424/330 |
| 4,171,370 | 10/1979 | Jonas et al. | 564/349 |
| 4,258,062 | 3/1981 | Jonas et al. | 424/330 |
| 4,311,708 | 1/1982 | Manoury et al. | 424/330 |

OTHER PUBLICATIONS

Brit. J. Ophthalmology (1977), pp. 301–303, Bonomi et al.
Chem. Abst. 81, 131068(y), (1974), Stankiewicz et al.

Primary Examiner—Douglas W. Robinson
Attorney, Agent, or Firm—Millen & White

[57] ABSTRACT 1-(p-2-iso-propoxyethoxymethyl-phenoxy)-3-isopropylamino-propan-2-ol and its biocompatible salts are very useful in decreasing the intra-ocular pressure, e.g., to treat glaucoma.

10 Claims, No Drawings

1-(P-2-ISOPROPOXYETHOXYMETHYL-PHENOXY)-3-ISOPROPYLAMINO-PROPAN-2-OL FOR DECREASING THE INTRA-OCULAR PRESSURE AND AN OPHTHALMIC PREPARATION THEREOF

BACKGROUND OF THE INVENTION

The present invention relates to a new ophthalmic preparation, particularly for decreasing the intra-ocular pressure, containing 1-(p-2-isopropoxyethoxymethyl-phenoxy)-3-isopropylamino-propan-2-ol (I) and/or one of its biocompatible acid addition salts.

For decreasing the intra-ocular pressure and, thus, for treating glaucoma, pilocarpine and its salts are particularly used. These have undesired side effects, such as focusing difficulties, night blindness and reaction impairment. Thus, attempts have been made to employ other substances, particularly beta-receptor-blockers, such as timolol (compare Belgian Patent Specification No. 846,574) or bupranolol for the treatment of glaucoma. However, these are not free of disadvantages either. Pulmonary, cardiovascular and central nervous side-effects occur, and particularly bronchoconstriction.

SUMMARY OF THE INVENTION

It is an object of this invention to provide an ophthalmic preparation, particularly for decreasing the intra-ocular pressure and thus for treating glaucoma, which eliminates or greatly ameliorates the disadvantages of the known agents.

Upon further study of the specification and appended claims, further objects and advantages of this invention will become apparent to those skilled in the art.

These objects have been attained based on the finding that compound I and its biocompatible salts decrease the intra-ocular pressure in an outstanding manner, and, furthermore, are very well tolerated. Side-effects, particularly bronchoconstriction, occur either not at all or only to a very slight extent. No symptoms of irritation were observed on local use on the eye of rabbits in concentrations of up to 40 mg/ml (aqueous solution, fumarate).

Accordingly, this invention relates to compound I and its biocompatible salts for decreasing the intra-ocular pressure. The present invention further relates to an ophthalmic preparation containing I or one of its biocompatible salts. In addition, the invention relates to the use of I or one of its biocompatible salts for decreasing the intra-ocular pressure.

DETAILED DISCUSSION

The substance I and its biocompatible salts, particularly the fumarate which is preferred, are known from the German Laid-Open Specification No. 2,645,710 and corresponding U.S. Pat. Nos. 4,171,370 and 4,258,062, whose disclosures are incorporated by reference therein. In this reference, some of the pharmacological effects of these compounds are also described, particularly their effects as isoprenaline antagonists. However, from the data given there, it could not be expected that these compounds would decrease the intra-ocular pressure outstandingly well with very good tolerance at the same time.

Compound I has an asymmetric C atom and can thus exist in two optically active forms. Both forms can be used in accordance with this invention, as can their mixtures, particularly also the optically inactive racemate. The S(-) form is preferred.

Particularly suitable biocompatible salts of compound I are the acid addition salts. These are derived from inorganic acids, for example, from sulfuric acid, nitric acid, hydrohalic acids, such as hydrochloric acid or hydrobromic acid, phosphoric acids, such as orthophosphoric acid, sulfamic acid, and also from organic acids, in particular aliphatic, alicyclic, araliphatic, aromatic or heterocyclic, monobasic or dipolybasic carboxylic, sulfonic or sulfuric acids, for example, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid or ethanesulfonic acid, ethanedisulfonic acid, 2-hydroxyethanesulfonic acid, benzenesulfonic acid, p-toluenesulfonic acid, naphthalenesulfonic acid, and naphthalenedisulfonic acids, and laurylsulfuric acid.

Compound I and its biocompatible salts are preferably administered in the form of the usual pharmaceutical preparations, which are conventional for ophthalmic preparations, to decrease the intra-ocular pressure. For this purpose, I can be converted into a suitable form for administration together with at least one solid, liquid and/or semi-liquid vehicle or auxiliary, and, if appropriate, in combination with one or several other active agents.

These preparations can be used as ophthalmic agents in human or veterinary medicine. Vehicles which may be used include organic or inorganic substances which are suitable for topical application and do not react with the compounds, for example, water, mixtures of water with water-miscible substances such as alkanols (for example ethanol) and aralkanols (for example benzyl alcohol), vegetable oils, benzyl alcohols, polyalkylene glycols (for example polyethylene glycols), esters such as glycerine triacetate, ethyl oleate or isopropyl myristate, vaseline, cellulose derivatives, such as ethylcellulose or carboxymethylcellulose, and polyvinylpyrrolidone. For local use, solutions are particularly suitable, preferably in the form of eye drops, also emulsions, suspensions, creams or ointments, and also implants. These preparations can be sterilized and/or contain auxiliaries such as preserving, stabilizing and/or wetting agents, emulsifiers, salts for adjusting the osmotic pressure and/or the viscosity, and, if appropriate, buffer substances. If desired, they can also contain one or more other active agents, for example, one or more vitamins or other agents which decrease the intra-ocular pressure, such as pilocarpine.

As a rule, compound I and its biocompatible salts can be administered, in accordance with the invention, analogous to known ophthalmic preparations available commercially, particularly glaucoma agents based on beta-receptor-blockers such as timolol or bupranolol, as is described, for example, in the Belgian Patent Specification No. 846,574, whose disclosure is incorporated by reference herein.

Preferably, application as eye drops is carried out in the form of an aqueous solution, an aqueous (for example, isotonic) saline solution or an oily solution, in which the content of I, for example, is 0.1 to 50, preferably 5 to 20 mg/ml, and which has a pH of about 5.5 to 8.5, particularly 6.0 to 7.5.

When I is used in the form of the fumarate in aqueous solution (pH about 6.7), the addition of buffer salts is not necessary, but also not detrimental; suitable buffers which may be added include, for example, monosodium, disodium, monopotassium and dipotassium phosphate, sodium borate, boric acid, sodium acetate, mono-, di- or trisodium citrate.

The solutions can also contain preserving agents or antiseptics, for example, quaternary ammonium salts such as benzalkonium chloride, phenyl-mercury salts such as phenyl-mercury acetate, thiomersal, methyl or propyl p-hydroxybenzoate or benzyl alcohol. To raise the viscosity, the addition of, for example, cellulose derivatives, for example methylcellulose is suitable. For the human eye, the unit dose of I is preferably about 0.001 to 5 mg, in particular 0.005 to 2 mg.

In ointments or creams, the concentration of I is preferably between 0.05 and 1 percent by weight.

Examples of suitable implants are films based on biocompatible substances of high molecular weight, for example cellulose derivatives such as methyl-, carboxymethyl-, hydroxyethyl-, hydroxypropyl- and hydroxypropylmethylcellulose; polyacrylates such as salts of polyacrylic acid, polyethyl acrylate and polyacrylamide; natural substances such as gelatine, alginates and tragacanth; polyvinyl alcohol, polyvinylpyrrolidone and polyvinyl methyl ether; and polyethylene oxide. The films can also contain auxiliaries, for example, plasticizers, preserving agents or buffer substances. To improve the flexibility, the films, particularly those based on cellulose derivatives, can also contain water, as a rule about 1 to 40, preferably about 10 to 20 percent by weight.

The films can be prepared, for example, by dissolving the active agent together with the vehicle in an inert solvent, pouring the solution into a suitable mold with a large surface area and allowing the solvent to evaporate. It is also possible to melt a solid mixture of powdered active agents and vehicles in the absence of a solvent and to pour the melt out to form a film. The films can have, for example, thicknesses of about 0.25 to 15 mm, preferably 0.5 to 1.5 mm. The film containing I which is obtained can then be cut up in the desired manner, it being possible for the implants to have, for example, the form of squared, rectangles, circles, semicircles or quarter-circles or ovals. Those forms are preferred which produce as little irritation of the eye as possible.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

Solution (eye drops)

1 g of I fumarate and 0.01 g of benzalkonium chloride are dissolved in sterile distilled water and made up to 100 ml with water. The solution (pH 6.7) is used in the form of eye drops.

EXAMPLE 2

Ointment 1 g of I fumarate is mixed with 200 g of vaseline.

EXAMPLE 3

Solution (eye drops)

0.5 g of I hydrochloride, 1.2 g of sodium chloride and 0.002 g of phenyl-mercury acetate are dissolved in water, the pH is adjusted to 8.2 with sodium hydroxide solution and the solution is made up to 100 ml with water.

EXAMPLE 4

Solution (eye drops)

2 g of I methanesulfonate, 1 g of disodium hydrogen phosphate 12 hydrate, 0.002 g of phenyl-mercury acetate and 0.4 g of methylcellulose are dissolved in water, the pH is adjusted to 7.6 and the solution is made up of 100 ml with water.

EXAMPLE 5

Solution (eye drops)

1.5 g of I (base) and 1 g of benzyl alcohol are dissolved in groundnut oil and made up to 100 ml with groundnut oil.

EXAMPLE 6

Implant

A solution of 1 g of I fumarate and 12 g of hydroxypropylcellulose in 60 ml of methanol is poured into a Telfon plate, so that a thin film is formed after evaporation of the solvent at 20°. This is subsequently cut into small pieces of the desired size, which are stored for 3 hours in a humidity chamber (88% humidity at 30°) and then sterile wrapped individually. Each piece contains 5 mg of I fumarate.

The preceding example(s) can be repeated with similar success by substituting the generically or specifically described reactants and/or operating conditions of this invention for those used in the preceding example(s).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ophthalmic composition comprising intraocular pressure lowering amount of 1-(p-2-isopropoxyethoxymethyl-phenoxy)-3-isopropylamino-propan-2-ol or a physiologically acceptable salt thereof and an ophthalmically acceptable carrier, in the form of an eye drop solution, an eye ointment, or an ocular film insert.

2. An ophthalmic composition of claim 1 which is an eye drop solution.

3. An ophthalmic composition of claim 1 which is an eye ointment.

4. An ophthalmic composition of claim 1 which is an ocular film insert.

5. An ophthalmic composition of claim 2 wherein the amount of active compound is 0.1–50 mg/ml and has a pH of 5.5–8.5.

6. A ophthalmic composition of claim 1 wherein the active agent is a fumarate salt.

7. A ophthalmic composition of claim 3 wherein the amount of active compound is 0.05 to 1 percent by weight.

8. An ophthalmic kit comprising an eye drop solution of claim 2 and an eye dropper.

9. A method of decreasing the intra-ocular pressure in a patient in need of such treatment comprising administering topically an ophthalmic composition of claim 1, 4, 5, 6 or 7 to the patient.

10. A method of claim 9 wherein the patient is suffering from glaucoma.

* * * * *